United States Patent
Cavalla et al.

(10) Patent No.: US 7,220,748 B2
(45) Date of Patent: May 22, 2007

(54) USE OF 4-(2-FLUROPHENYL)-6-METHYL-2-(1-PIPERAZINYL)THIENO(2,3-D)-PYRIMIDINE FOR TREATING OF URINARY INCONTINENCE

(75) Inventors: David Cavalla, Cambridge (GB); Robert William Gristwood, Cambridge (GB)

(73) Assignee: Arachnova Therapeutics Ltd., Jersey (GB)

( * ) Notice: Subject to any disclaimer, the term of this patent is extended or adjusted under 35 U.S.C. 154(b) by 0 days.

(21) Appl. No.: 10/502,827

(22) PCT Filed: Jan. 29, 2003

(86) PCT No.: PCT/GB03/00374

§ 371 (c)(1),
(2), (4) Date: Jul. 27, 2004

(87) PCT Pub. No.: WO03/063873

PCT Pub. Date: Aug. 7, 2003

(65) Prior Publication Data

US 2005/0222162 A1    Oct. 6, 2005

(30) Foreign Application Priority Data

Jan. 31, 2002    (GB) .................. 0202265.5

(51) Int. Cl.
*A61K 31/4965*    (2006.01)
*C07D 417/04*    (2006.01)
(52) U.S. Cl. ..................... 514/255; 544/362
(58) Field of Classification Search ............... 544/362; 514/255
See application file for complete search history.

(56) References Cited

U.S. PATENT DOCUMENTS 5,744,474 A    4/1998    Thor

FOREIGN PATENT DOCUMENTS

EP    0 467 365 A2    1/1992

OTHER PUBLICATIONS

Chen, Hong-I (Sep. 1990) Evidence for the presynaptic action of 5-hydroxytryptamine and the involvement of purinergic innervation in the rabbit lower urinary tract *Br. J. Pharmacol.* 101:212-216.
Eguchi, Junichi et al. (Apr. 2001) "The anxiolytic-like effect of MCI-225, a selective NA reuptake inhibitor with 5-$HT_3$ receptor antagonism" *Pharmacology, Biochemistry and Behavior* 68:677-683.
Eguchi, Junichi et al. (1997) "Pharmacological Profile of the Novel Antidepressant 4-(2-Fluorophenyl)-6-methyl-2-(1-piperazinyl)thieno-[2,3-d]pyrimidine Monohydrate Hydrochloride" *Arzneimittel-Forschung/Drug Research* 47(II), 12, 1337-1347.
Espey, Mary Jane et al. (1998) "Serotonergic modulation of spinal ascending activity and sacral reflux activity evoked by pelvic nerve stimulation in cats" *Brain Research* 798:101-108.
Espey, Mary Jane and John W. Downie (1995) "Serotonergic modulation of cat bladder function before and after spinal transaction" *European Journal of Pharmacology* 287:173-177.
Database Biosis 'Online!, Wu Ying-Liang et al. "Effects of acute and chronic administration of MCI-225, a new selective moradrenaline reuptake inhibitor with 5-HT3 receptor blocking action, on extraceullar noradrenaline levels in the hypothalamus of stressed rats" Database accession No. PREV200000291518, abstract, Japanese Journal of Pharmacology, vol. 83, No. 1, May 2000 pp. 31-18.

*Primary Examiner*—Rita Desai
(74) *Attorney, Agent, or Firm*—Saliwanchik Lloyd & Saliwanchik

(57) ABSTRACT

4-(2-Fluorophenyl)-6-Methyl-2-(1-Piperazinyl)-Thieno(2,3-D)pyrimidine or a salt thereof is useful for the treatment of urinary incontinence.

3 Claims, No Drawings

USE OF 4-(2-FLUROPHENYL)-6-METHYL-2-(1-PIPERAZINYL)THIENO(2,3-D)-PYRIMIDINE FOR TREATING OF URINARY INCONTINENCE

This application is a National Stage Application of International Application Number PCT/GB03/00374, filed Jan. 29, 2003; which claims priority to Great Britain Application GB 0202265.5, filed Jan. 31, 2002.

FIELD OF THE INVENTION

This invention relates to a new therapeutic use for a known compound.

BACKGROUND OF THE INVENTION 4-(2-Fluorophenyl)-6-methyl-2-(1-piperazinyl)thieno[2,3-D]pyrimidine monohydrate hydrochloride is known (see U.S. Pat. No. 4,695,568) and has shown activity as an antidepressant. It has serotonin and noradrenergic reuptake blocking properties and this is thought to be the mechanism for its action as an antidepressant. The compound also has 5HT-3 receptor blocking activity.

Urinary incontinence is a distressing condition which is poorly treated. It can be classified as urge (caused by overactive bladder) or stress (for example caused by prolapse of the bladder to a position which puts excessive pressure on the urethral sphincter). Some unfortunate patients have both of these types of urinary incontinence which is known as mixed. Other types of urinary incontinence have been described, including functional incontinence, overflow incontinence and transient incontinence (a temporary condition due to infection or medication). Urinary incontinence can be caused by a number of disorders.

All of the drugs used for incontinence have side effect problems which often result in non-compliance with treatment or a necessary withdrawal of treatment. Also they are not always effective. For stress incontinence, surgery is often the only answer although an antidepressant that is a serotonin and noradrenaline reuptake blocker, duloxetine, is showing some promise in clinical trials. Other antidepressants have also shown activity in in vivo models of urinary incontinence (see U.S. Pat. No. 5,744,474).

SUMMARY OF THE INVENTION

Surprisingly, it has been found that the known compound identified above (referred to herein as MCI-225) has activity in the treatment of urinary incontinence. Its combination of serotonin and noradrenergic reuptake blockade and 5HT-3 receptor blockade has not properly been identified as being responsible for activity in incontinence. Furthermore MCI-225, at doses effective in the treatment of urinary incontinence, can produce a lower incidence of some of the side-effects which are commonly known to be associated with the clinical use of selective serotonin reuptake inhibitors, for example the production of nausea and vomiting or the induction of sexual dysfunction. It will be appreciated that any suitable form of the active principle may be used, e.g. another salt form, or a prodrug or active metabolite.

DESCRIPTION OF THE INVENTION

By means of this invention, incontinence can be treated, e.g. controlled or prevented. For this purpose, the active compound can be formulated in any suitable manner together with a conventional diluent or carrier. The active compound is preferably administered by the oral route; other suitable routes of administration include sublingual/buccal, transdermal, intramuscular, intranasal, rectal, parenteral, subcutaneous, pulmonary and topical. The dose of the active agent will depend on the nature and degree of the complaint, the age and condition of the patient and other factors known to those skilled in the art. A typical daily dosage may be 0.1 mg to 1000 mg.

A pharmaceutical composition containing the active ingredient may be in the form of a sublingual tablet or patch. Suitable compositions for oral use include tablets, troches, lozenges, aqueous or oily suspensions, dispersible powders or granules, emulsions, hard or soft capsules, syrups and elixirs. Suitable additives include sweetening agents, flavouring agents, colouring agents and preserving agents. Tablets contain the active ingredient in admixture with non-toxic pharmaceutically acceptable excipients, e.g. inert diluents such as calcium carbonate, sodium carbonate, lactose, calcium phosphate or sodium phosphate; granulating and disintegrating agents, for example corn starch or alginic acid; binding agents, for example starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated, to form osmotic therapeutic tablets for controlled release. Hard gelatin capsules may include an inert solid diluent, for example calcium carbonate, calcium phosphate or kaolin; soft gelatin capsules may include water or an oil medium, for example peanut oil, liquid paraffin or olive oil.

The data on which this invention is based will now be described. In a study, using intact animals, the ability of MCI-225 to increase the tone of the urethra/internal sphincter (a desired effect for the treatment of stress urinary incontinence) was assessed. The results show that MCI-225 is able to increase the smooth muscle tone of the lower urinary tract and will thus be of clinical utility in urinary incontinence.

Study

Female Sprague-Dawley rats (225–350 g) were anaesthetised using urethane. The bladder was exposed through a midline incision into the abdomen and intravesicular pressure was recorded via a catheter inserted into the bladder. A second catheter was inserted into the bladder to allow infusion of saline using a syringe pump when required. A third catheter was inserted into the bladder and wedged into position in the neck of the bladder with the catheter extending into the urethra. This set-up allowed constant infusion of saline into the urethra whilst urethral pressure was recorded. Changes in urethral pressure are assumed to reflect changes in urethral resistance. In each animal, electromyographic (EMG) recordings were made of urethral striated muscle activity by inserting 2 fine copper electrodes either side of the urethral opening.

Once stable, bladder and urethral pressures were recorded, the bladder was inflated by direct infusion of physiological saline into the bladder at a rate of 0.046 ml/min. This rate approximates the maximum hourly diuresis rate. Infusion into the bladder was terminated prior to evoking micturition and the bladder volume maintained. During and after saline infusion, simultaneous recordings were made of urethral perfusion pressure and of external sphincter EMG activity. Once these parameters had stabilised, autonomic drive to the lower urinary tract was inhibited by administration of hexamethonium (10 mg/kg i.v.) and changes to urethral perfusion pressure and external sphincter EMG recorded. Decamethonium (30 mg/kg i.v.) was then added to remove striated muscle activity. In one group of animals, prior to intravesicular infusion of saline a single bolus dose of MCI-225 was administered (3 mg/kg i.v.). In a second group of animals a bolus dose of vehicle was administered. The effect of MCI-225 and vehicle was determined by analysing the changes in urethral perfusion pressure and external sphincter EMG activity during and after infusion and following administration of the ganglion blocker hexamethonium and then finally decamethonium to block the striated muscle activity of the external sphincter.

Results are shown in Tables 1 and 2. They show that MCI-225 caused a rise in urethral pressure from 13±1 mmHg to 23±2 mmHg, an increase of 77%. The vehicle control on the other hand caused a rise in urethral pressure from 14±1 mmHg to 18±2 mmHg, an increase of only 29%. The rise in pressure caused by MCI-225 was statistically significant (p=0.04 Students t test) whereas the rise with control was not. This implies that the administration of MCI-225 increased the tone of the urethra/internal sphincter, a desired effect for the treatment of urinary incontinence.

Also of importance are the results seen when hexamethonium was administered to the animals. Inhibition of the autonomic nervous system with hexamethonium caused a fall in urethral perfusion pressure, and the magnitude of the drop identified the extent to which urethra/internal sphincter tone (due to autonomic nervous system activity) was contributing to outlet resistance. The drop seen in MCI-225-treated animals (55±5%) was greater than vehicle-treated animals (35±7%). Larger falls in external sphincter activity (EUS-EMG) were seen in MCI-225-treated animals. These results imply that the administration of MCI-225 had increased the tone of urethra/internal sphincter, the desired effect for the treatment of stress urinary incontinence.

When decamethonium was administered there were some further small decreases in urethral perfusion pressure; decreases from values measured before hexamethonium administration were 64±7% and 44±4% for MCI-225 and vehicle-treated animals respectively.

TABLE 1

Baseline values for mean arterial blood pressure (MAP), heart rate (HR) and urethral perfusion pressure (UP) in anaesthetized female rats.

|  | n | MAP (mmHg) | HR (beats min$^{-1}$) | UP (mmHg) |
|---|---|---|---|---|
| Control | 3 | 104 ± 3 | 375 ± 12 | 14 ± 1 |
| MCI-225 (3 mg kg$^{-1}$) | 3 | 105 ± 6 | 405 ± 15 | 13 ± 2 |

TABLE 2

Values of vesicular pressure (VP) and urethral perfusion pressure (UP) after intravesicular infusion in anaesthetized female rats.

|  | n | VP (mmHg) | UP (mmHg) |
|---|---|---|---|
| Control | 3 | 9 ± 2 | 18 ± 2 |
| MCI-225 (3 mg kg$^{-1}$) | 3 | 8 ± 1 | 23 ± 2 |

The invention claimed is:

1. A method for treating urinary incontinence wherein said method comprises administering, to a patient in need of such treatment, an effective amount of 4-(2-fluorophenyl)-6-methyl-2-(1-piperazinyl)thieno[2,3-D]pyrimidine or a salt thereof.

2. The method, according to claim 1, wherein the salt is the monohydrate hydrochloride.

3. The method, according to claim 1, wherein the urinary incontinence is stress urinary incontinence.

* * * * *

UNITED STATES PATENT AND TRADEMARK OFFICE
CERTIFICATE OF CORRECTION

PATENT NO. : 7,220,748 B2  Page 1 of 1
APPLICATION NO. : 10/502827
DATED : May 22, 2007
INVENTOR(S) : David Cavalla and Robert William Gristwood It is certified that error appears in the above-identified patent and that said Letters Patent is hereby corrected as shown below:

On the Title Page, Item (54),

Line 1, "(2-FLUROPHENYL)" should read --(2-FLUOROPHENYL)--.

Signed and Sealed this

Twenty-seventh Day of November, 2007

JON W. DUDAS
*Director of the United States Patent and Trademark Office*